(12) United States Patent
Appenzeller et al.

(10) Patent No.: US 8,419,735 B2
(45) Date of Patent: Apr. 16, 2013

(54) NAIL LOCKING SYSTEMS

(75) Inventors: Andreas Appenzeller, Biel (CH); Robert Frigg, Bettlach (CH); Nicolas Bouduban, Bruegg (CH); Ladislav Nagy, Kilchberg (CH)

(73) Assignee: Synthes USA, LLC, West Chester, PA (US)

( * ) Notice: Subject to any disclaimer, the term of this patent is extended or adjusted under 35 U.S.C. 154(b) by 194 days.

(21) Appl. No.: 12/773,373

(22) Filed: May 4, 2010

(65) Prior Publication Data

US 2011/0112534 A1 May 12, 2011

Related U.S. Application Data

(60) Provisional application No. 61/175,555, filed on May 5, 2009.

(51) Int. Cl.
*A61B 17/72* (2006.01)
*A61B 17/88* (2006.01)

(52) U.S. Cl.
USPC ............................................................ 606/64

(58) Field of Classification Search ............. 606/74–75, 606/62–68, 280–331, 70–71
See application file for complete search history.

(56) References Cited

U.S. PATENT DOCUMENTS

| | | | |
|---|---|---|---|
| 4,978,349 A | 12/1990 | Frigg | |
| 5,603,715 A | 2/1997 | Kessler | |
| 6,270,499 B1 | 8/2001 | Leu et al. | |
| 6,344,042 B1* | 2/2002 | Curtis et al. | 606/298 |
| 7,341,590 B2* | 3/2008 | Ferree | 606/915 |
| 7,632,272 B2 | 12/2009 | Munro et al. | |
| 2003/0097131 A1* | 5/2003 | Schon et al. | 606/62 |
| 2005/0038435 A1* | 2/2005 | Cole et al. | 606/64 |
| 2006/0106385 A1* | 5/2006 | Pennig | 606/64 |
| 2006/0122600 A1* | 6/2006 | Cole | 606/62 |
| 2008/0091203 A1* | 4/2008 | Warburton et al. | 606/62 |
| 2008/0140127 A1* | 6/2008 | Vasta et al. | 606/280 |
| 2008/0154311 A1 | 6/2008 | Staeubli | |
| 2009/0062796 A1* | 3/2009 | Parks et al. | 606/62 |
| 2009/0069812 A1* | 3/2009 | Gillard et al. | 606/62 |
| 2009/0177240 A1* | 7/2009 | Perez | 606/86 R |
| 2009/0306664 A1* | 12/2009 | Teeny | 606/64 |
| 2010/0137863 A1* | 6/2010 | Munro | 606/64 |
| 2011/0190769 A1* | 8/2011 | Haininger | 606/64 |

FOREIGN PATENT DOCUMENTS

| | | |
|---|---|---|
| DE | 3144210 | 5/1983 |
| EP | 1 398 000 | 3/2004 |
| EP | 1 952 776 | 8/2008 |
| FR | 2658715 | 8/1991 |
| WO | 2009/042783 | 4/2009 |

* cited by examiner

*Primary Examiner* — Ellen C Hammond
*Assistant Examiner* — Jacqueline Johanas
(74) *Attorney, Agent, or Firm* — Fay, Kaplun & Marcin, LLP

(57) ABSTRACT

A system for fixing a fracture near a joint of a bone comprises (a) an intramedullary device including a longitudinal body and a head, the longitudinal body extending from a proximal end to a distal end, the head being attached to the proximal end of the longitudinal body; and (b) a plate implantable into a head portion of the bone to provide support to a joint zone, the plate engageable with the intramedullary device. The plate is substantially U-shaped and includes a midsection and a pair of arms extending from the midsection, the pair of arms forming a space therebetween, the space sized and shaped to accommodate the head of the intramedullary device.

23 Claims, 7 Drawing Sheets

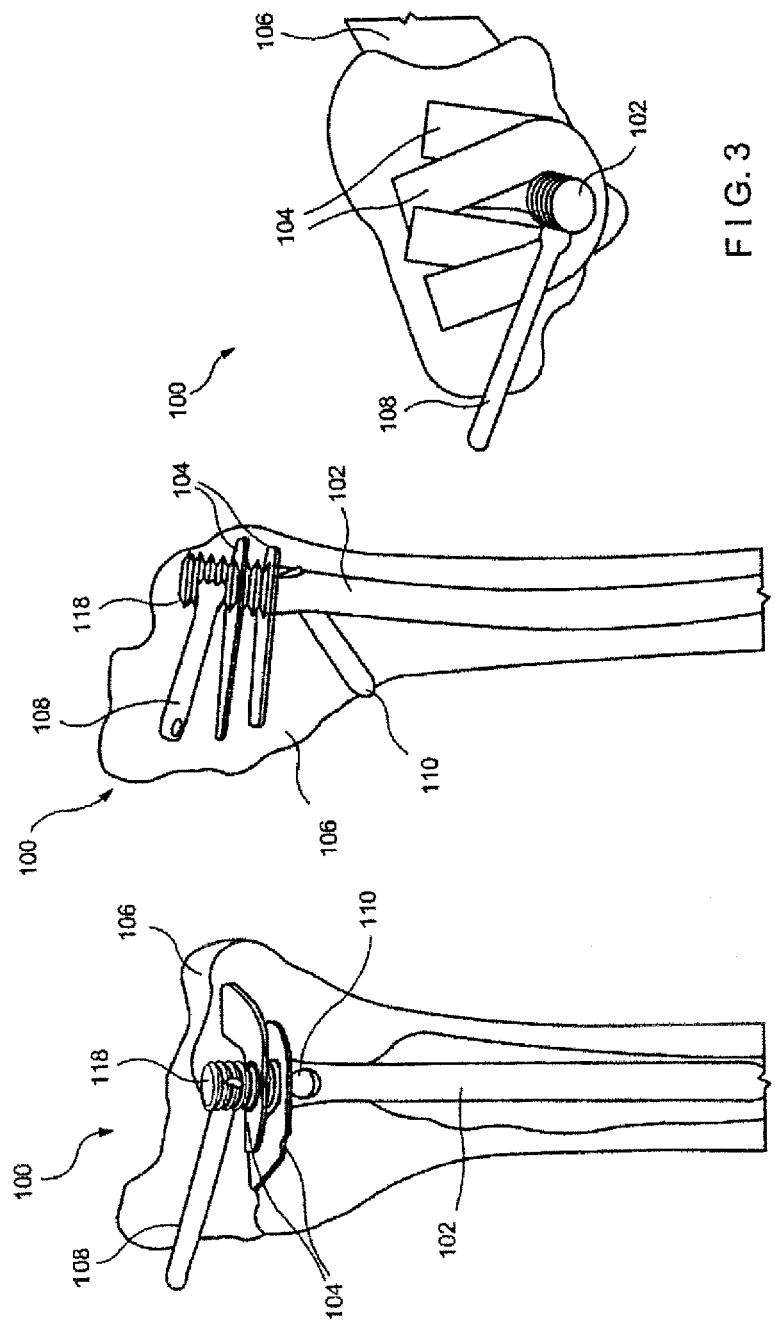

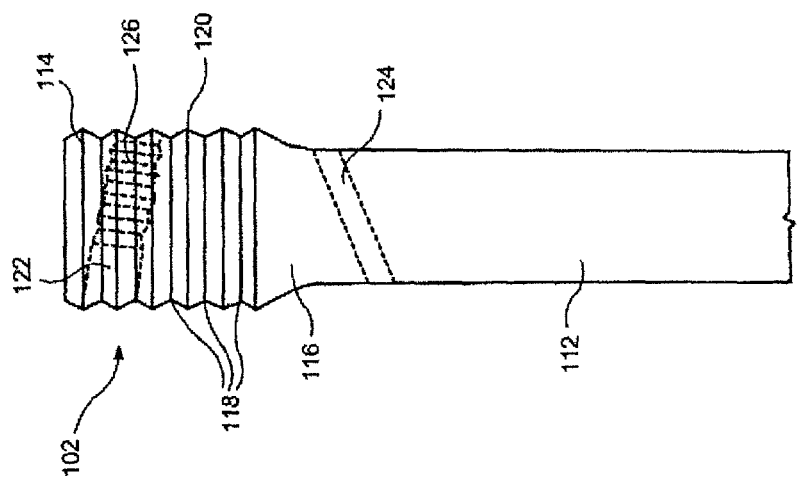
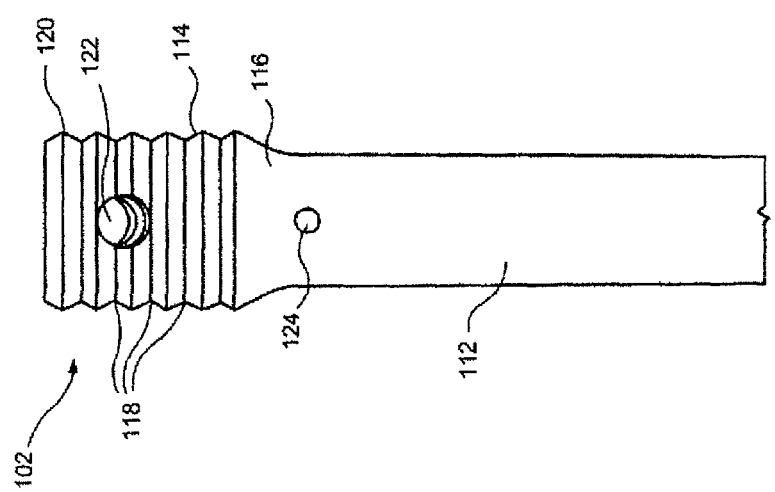

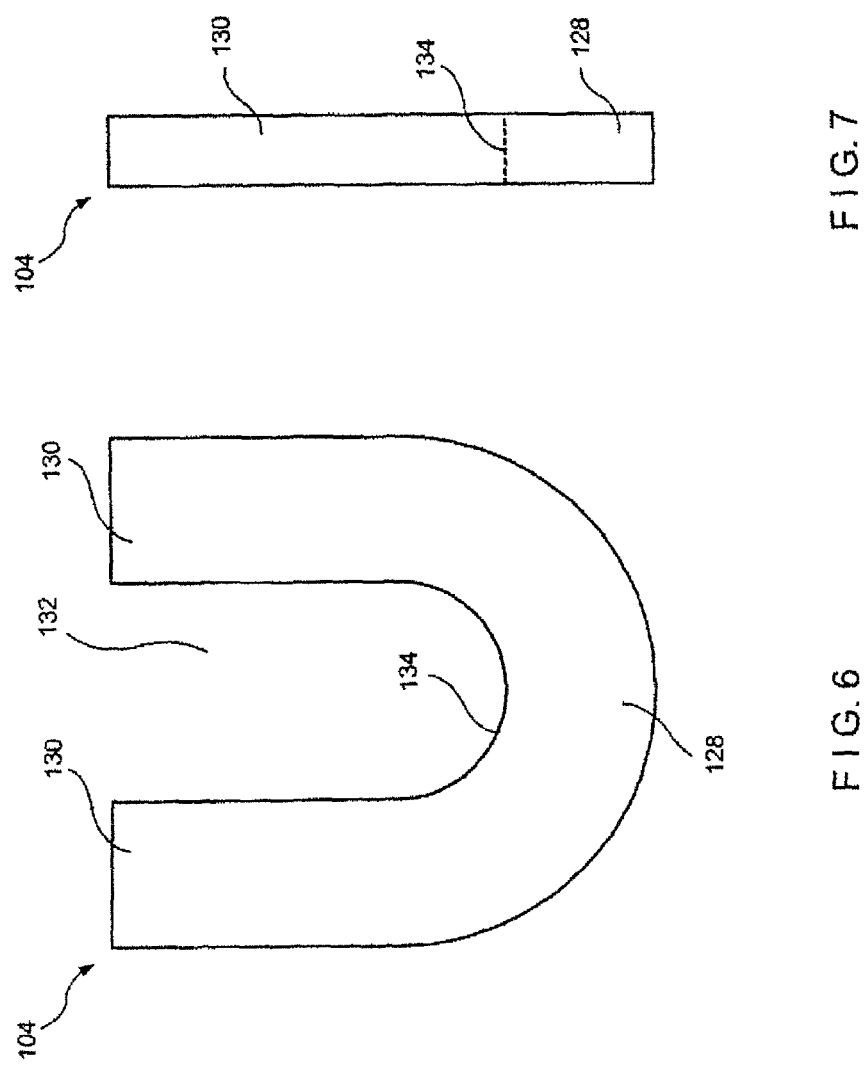

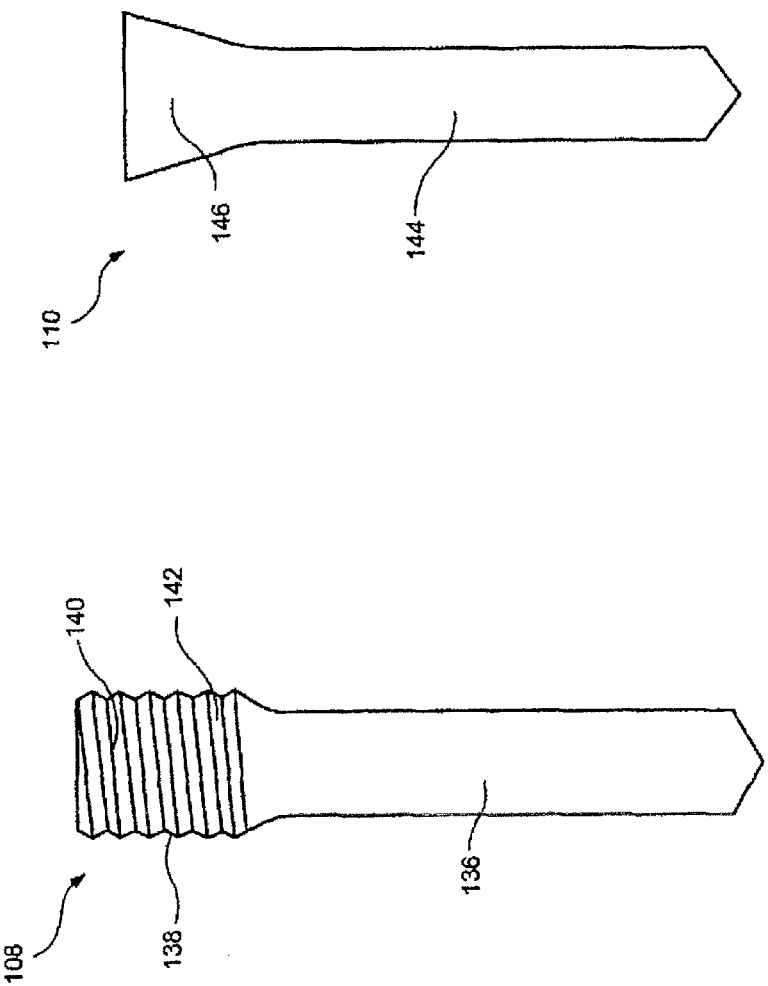

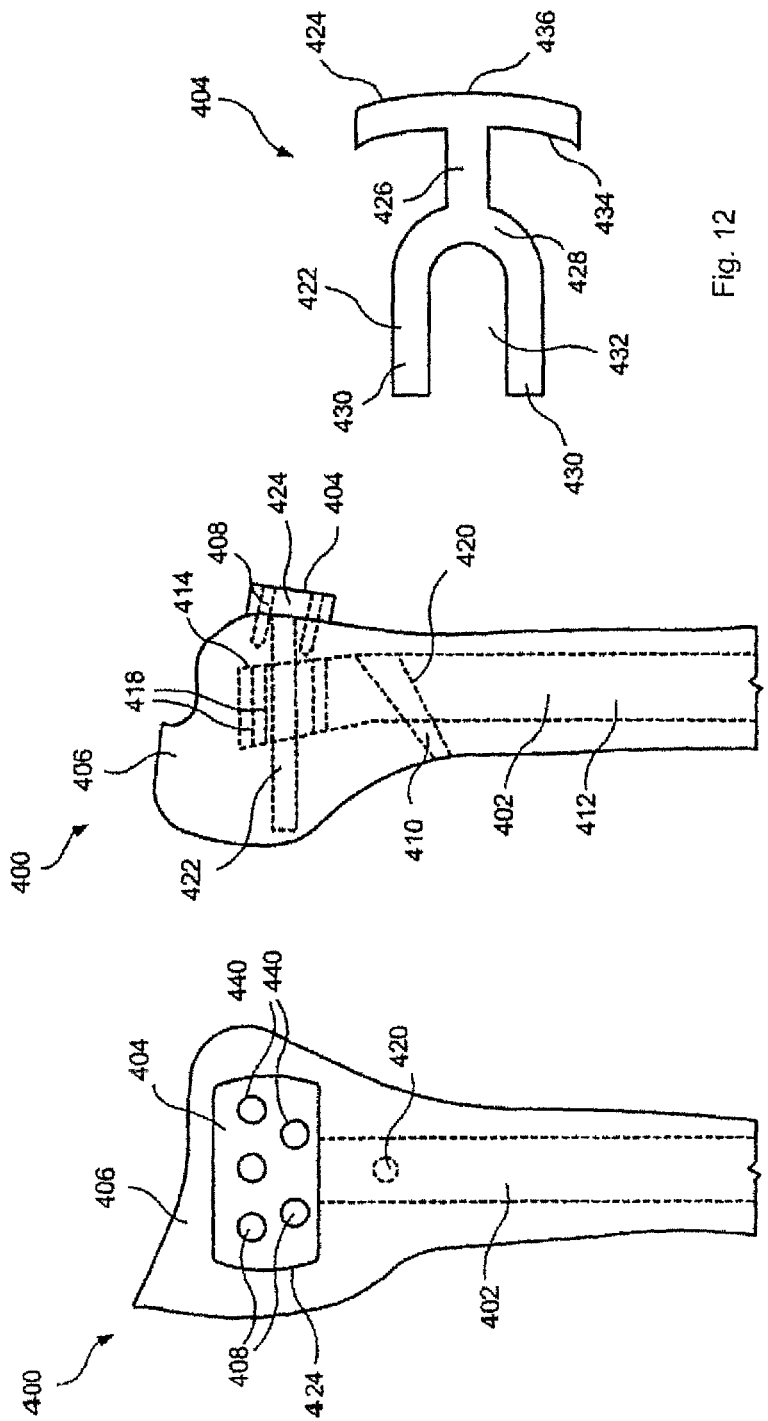

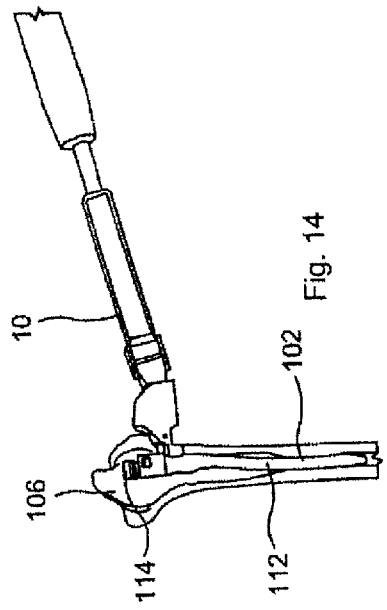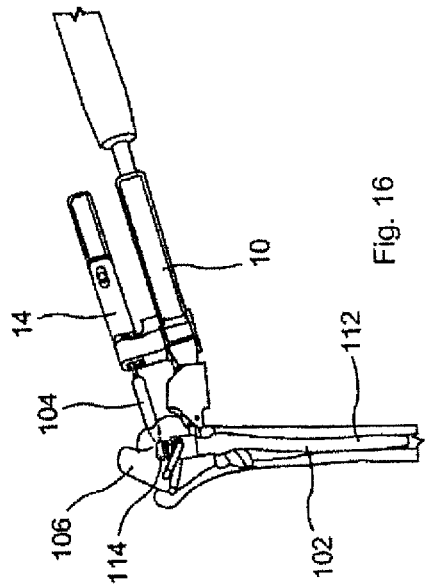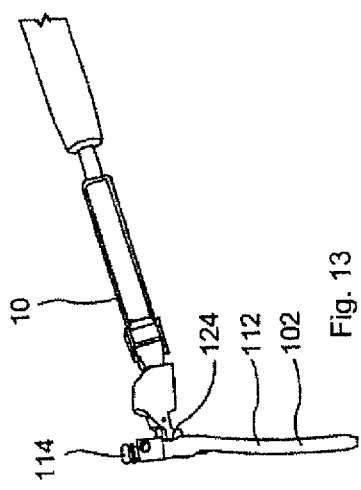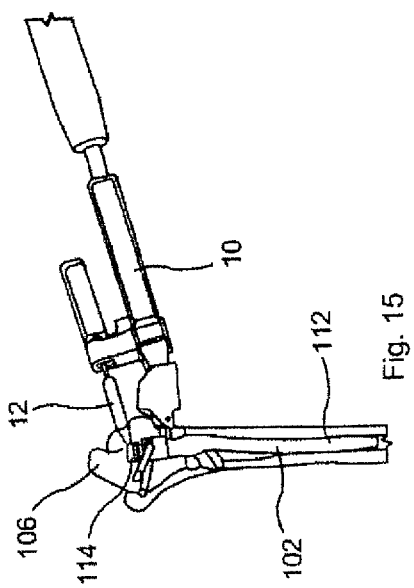

NAIL LOCKING SYSTEMS

PRIORITY CLAIM

The present application claims priority to U.S. Provisional Application Ser. No. 61/175,555 filed on May 5, 2009 entitled "Nail Locking Systems," the entire disclosure of which is incorporated herein by reference

BACKGROUND

The present invention relates to systems for bone fixation and, in particular, to an intramedullary metaphyseal fracture stabilization system.

A fracture in the shaft of a long bone may be treated by the insertion of an intramedullary nail or other device into the medullary canal. Intramedullary fracture fixation is advantageous because it provides stability along a length of the bone. A fracture near a joint such as, for example, a fracture in a metaphyseal zone, however, is generally fixed with screws and plates rather than intramedullary devices. The use of screws and plates alone, however, reduces the support and stability of the bone, which may result in a fracture collapse from forces or pressures exerted on the bone.

SUMMARY OF THE INVENTION

The present invention relates to a system for fixing a fracture near a joint of a bone. The system comprises (a) an intramedullary device including a longitudinal body and a head, the longitudinal body extending from a proximal end to a distal end, the head being attached to the proximal end of the longitudinal body; and (b) a plate implantable into a head portion of the bone to provide support to a joint zone, the plate engagable with the intramedullary device. The plate is substantially U-shaped and includes a midsection and a pair of arms extending from the midsection, the pair of arms forming a space therebetween, the space sized and shaped to accommodate the head of the intramedullary device.

In a special embodiment the plate includes a first portion implantable into the bone and a second portion fixable to a surface of the bone, the first portion being substantially U-shaped and including a midsection and a pair of arms extending from the midsection, the pair of arms forming a space therebetween to accommodate the head of the intramedullary device, the second portion being sized and shaped to fix a fracture of the bone.

In a further embodiment the first portion of the plate lies in a plane substantially perpendicular to a plane in which the second portion is lying.

In again a further embodiment the second portion includes a plurality of openings, the plurality of openings sized and shaped to accommodate bone fixation elements therethrough.

In another embodiment the head of the intramedullary device includes a plurality of recesses, each recess extending about at least a portion of a perimeter of the head, the recess being sized and shaped to accommodate an inner surface of the plate, preferably at the midsection between said pair of arms.

In another embodiment the intramedullary device has one or more openings extending laterally through the head of the intramedullary device.

In yet another embodiment said system further comprises a bone fixation element insertable into the opening of the intramedullary device to fix a fracture of the bone.

In again another embodiment the bone fixation element is a locking head screw and the opening of the intramedullary device preferably has a thread.

In yet another embodiment said intramedullary device has at least two openings whose central axes are not parallel to each other and preferably are flaring outwardly or converging for providing support to the joint surface.

In a further embodiment said plate has an upper and a lower surface which together have a surface area of 190 to 320 mm$^2$, preferably 210 to 270 mm$^2$. Typically, said upper and lower surface together have a surface area of 2×120 mm$^2$=240 mm$^2$.

In a further embodiment said plate has—measured in the plane of the plate—a minimum diameter of two times, preferably three times the diameter of the intramedullary device. Typically, said minimum diameter of said plate is 12 mm.

In again a further embodiment said plate has means for clipping the plate to the intramedullary device.

In another embodiment said pair of arms of said plate is configured as a snap-on mounting, preferably as a circlip ring. Said pair of arms including said circlip ring can be configured similarly to a Seeger circlip ring.

In another embodiment the system comprises several plates engageable with the intramedullary device on different heights of the intramedullary device whose arms are preferably oriented in different directions.

In again another embodiment said intramedullary device is an intramedullary nail, preferably with one or more transverse locking holes.

In accordance with another aspect of the invention, a method is provided which comprises:

inserting an intramedullary device into a medullary canal of the bone via a fracture zone of the bone, the intramedullary device including a longitudinal body and a head, the longitudinal body extending from a proximal end to a distal end, the head being attached to the proximal end of the longitudinal body;

implanting a substantially U-shaped plate, including a midsection and a pair of arms extending from the midsection, the pair of arms forming a space therebetween, into the bone so that the pair of arms forming a space therebetween engagingly accommodate the head of the intramedullary device.

In a special embodiment of the method said plate is clipped or secured to said intramedullary device.

In another embodiment of the method several plates are engaged with the intramedullary device on different heights of the intramedullary device

BRIEF DESCRIPTION OF THE DRAWINGS

FIG. 1 illustrates a side perspective view of a system according to a first exemplary embodiment of the present invention;

FIG. 2 illustrates another side perspective view of the system of FIG. 1, rotated 90 degrees about a longitudinal axis of the system;

FIG. 3 illustrates a top perspective view of the system of FIG. 1;

FIG. 4 illustrates a side view of an intramedullary device according to the system of FIG. 1;

FIG. 5 illustrates another side view of the intramedullary device of FIG. 4, rotated 90 degrees about a longitudinal axis thereof;

FIG. 6 illustrates a top view of a plate according to the system of FIG. 1;

FIG. 7 illustrates a side view of the plate of FIG. 6;

FIG. 8 illustrates a side view of a first bone fixation element according to the system of FIG. 1;

FIG. 9 illustrates a side view of a second bone fixation element according to the system of FIG. 1;

FIG. 10 illustrates a side view of a system according to a second exemplary embodiment of the present invention;

FIG. 11 illustrates another side view of the system of FIG. 10, rotated 90 degrees about a longitudinal axis thereof;

FIG. 12 illustrates a top view of a plate according to the system of FIG. 10;

FIG. 13 illustrates a side view of an embodiment of the intramedullary device according to the invention coupled to a guiding device used in an embodiment of a surgical technique according to the invention;

FIG. 14 illustrates a side view of the embodiment of the intramedullary device of FIG. 13 inserted into the medullary channel;

FIG. 15 illustrates a side view of the embodiment of the intramedullary device of FIG. 13 during preparation for implantation of the plates;

FIG. 16 illustrates a side view of the embodiment of the intramedullary device of FIG. 13 during insertion of a plate;

DETAILED DESCRIPTION

Figure 18:
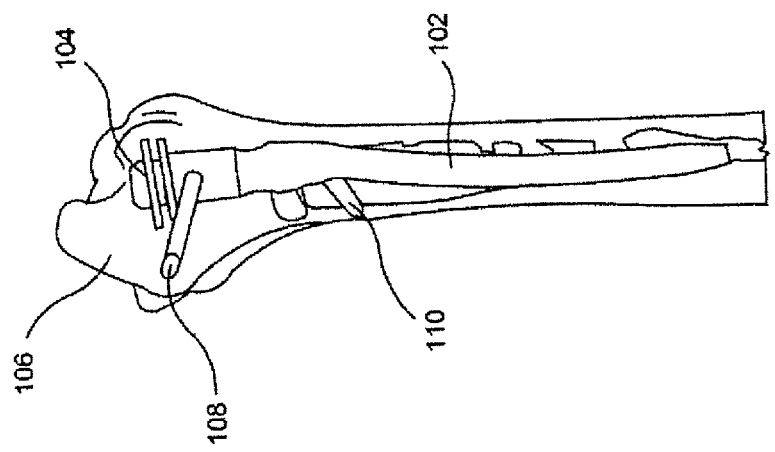
FIG. 18 illustrates a side view of the embodiment of the intramedullary device of FIG. 13 after removal of the guiding device.

The present invention may be further understood with reference to the following description and the appended drawings, wherein like elements are referred to with the same reference numerals. The present invention relates to systems for bone fixation. In particular, exemplary embodiments of the present invention describe an intramedullary metaphyseal fracture stabilization system. It should be noted however, that the present invention is not limited to metaphyseal fractures. For example, it will be understood by those of skill in the art that the exemplary embodiments of the present invention may also be used to stabilize a diaphyseal fractures by inserting an additional bone fixation element, such as a screw, in the diaphyseal zone. It should also be noted that the use of the terms proximal and distal do not refer to a specific direction, but are used to refer to a direction toward (proximal) and away from (distal) a surgeon or other user of the system.

As shown in FIGS. 1-3, a system 100 according to the present invention is adapted for the treatment of fractures near joints and comprises an intramedullary device 102 sized and shaped for insertion into a medullary canal of a bone 106, and at least one plate 104 insertable into a fracture zone of the bone 106. The plate 104 engages the intramedullary device 102 so that the plate 104 provides support to the joint area like a stabilization plateau. The system 100 further comprises first and second bone fixation elements 108, 110, respectively, with the first bone fixation element 108 stabilizing a fractured portion of the bone 106 while the second bone fixation element 110 fixes the intramedullary device 102 at a desired position within the medullary canal of the bone 106.

As shown in FIG. 4, the intramedullary device 102 includes a longitudinal body 112 and a head 114 attached to a proximal end 116 of the longitudinal body 112. The head 114 includes a plurality of recesses 118 on an outer surface 120 of the head 114, each of the plurality of recesses 118 extending about at least a portion of a perimeter of the head 120 to engage the plate 104. The intramedullary device 102 may further include a first opening 122 extending laterally through the head 114 to accommodate the first bone fixation element 108. The first opening 122 may extend through the head 114 substantially perpendicularly to a longitudinal axis of the intramedullary device 102. Alternatively, the first opening 122 may extend through the head 114 at a non-perpendicular angle relative to the longitudinal axis as shown in FIG. 5. In a preferred embodiment, the first opening 122 may be angled at approximately 30 degrees relative to the longitudinal axis, but may deviate from this angle by up to 15 degrees. The angle of the first opening 122 may be selected to correspond, for example, to a position of a fracture to be treated. Additionally, the first opening 122 may include a threading 126 along an inner surface thereof for engaging a portion of the first bone fixation element 108. It will be understood by those of skill in the art that the head 114 of the intramedullary device 102 may include more than one first opening 122.

The intramedullary device 102 may also include one or more second openings 124 extending laterally through the longitudinal body 112 and located along a length of the longitudinal body 112. Each second opening 124 is sized and shaped to accommodate the second bone fixation element 110, which fixes the intramedullary device 102 at a desired position within the medullary canal of the bone 106. The second opening 124 may extend through the longitudinal body 112 at an angle relative to the longitudinal axis of the intramedullary device 102. In a preferred embodiment, the second opening 124 may be angled at approximately −30 degrees relative to the longitudinal axis, but may deviate from this angle by up to "15 degrees, to provide additional stability for the second bone fixation element 110 inserted therethrough. In a preferred embodiment, the second opening 124 may be located at the proximal end 116 of the longitudinal body 112. However, it will be understood by those of skill in the art that the second opening 124 may be located anywhere along a length of the longitudinal body 112. It will also be understood by those of skill in the art that the intramedullary device 102 may include more than one second opening 124.

In a preferred embodiment, as shown in FIGS. 5-6, the plate 104 may be substantially U-shaped such that a pair of arms 130 extend from a midsection 128. The pair of arms 130 and the midsection 128 may be integrally formed as a single unitary construction. The arms 130 extend from the midsection 128 forming a space 132 between the pair of arms 130. The space 132 is preferably sized and shaped to accommodate a width of the head 114 of the intramedullary device 102. An inner surface 134 of the midsection 128 is sized and shaped to be accommodated in one of the recesses 118 of the head 114 to lock the plate 104 in a desired position relative to the head 114. A length and/or a width of each of the arms 130 may vary depending on a desired angular orientation relative to the longitudinal axis of the intramedullary device 102. It will be understood by those of skill in the art that the U-shape provides wide support of the joint zone, minimizing the possibility of bone splintering. However, it will also be understood by those of skill in the art that a variety of shapes may be utilized for the plate 104 so long as the plate 104 is engagable with one of the recesses 118 of the head 114. For example, the plate 104 may be asymmetrical such that one of the pair of arms 130 is longer than the other. Alternatively, the plate 104 may include the midsection 128 and only one arm 130 extending from an end thereof. It will also be understood by those of skill in the art that more than one plate 104 may be employed with the system 100.

As shown in FIG. 8, the first bone fixation element 108 may be any standard bone fixation element that is insertable through the first opening 122. The first bone fixation element 108 may be, for example, a screw or a pin, including a shaft 136 and a head 138. The head 138 may include a threading 140 along an outer surface 142 thereof for engaging with the threading 126 of the opening 122. Thus, the head 138 of the first bone fixation element 108 may be locked to the intramedullary device 102 such that the shaft 136 may fix the fracture in the bone relative to the medullary canal. It will be understood by those of skill in the art that the shaft 136 may also include a threading along at least a portion of a length of the shaft 136. As described above, the first bone fixation element 108 may be fixed at an angle relative to the intramedullary device 102. It will also be understood by those of skill in the art that more than one first bone fixation element 108 may be employed with the system 100.

As shown in FIG. 9, the second bone fixation element 110 may also be any standard bone fixation element, such as, for example, a screw or pin, so long as the second bone fixation element 110 is capable of fixing the intramedullary device 102 at a desired position within the medullary canal of the bone 106. The second bone fixation element 110 may include a shaft 144 and a head 146, however, the head 146 is not required to be locked to the intramedullary device 102 and does not necessarily include a threading thereabout. As described above, the locking screw 108 may be fixed to the intramedullary device 102 at an angle relative to the longitudinal axis of the intramedullary device 102, providing additional stability to the intramedullary device 102. It will be understood by those of skill in the art that more than one second bone fixation element 110 may be employed with the system 100.

As shown in FIGS. 10-11, a system 400 according to an exemplary embodiment of the present invention comprises an intramedullary device 402 insertable into a medullary canal of a bone 406 and engagable with a plate 404. The system 400 further comprises a first bone fixation element 408 for coupling the plate 404 to the bone 406. The system 400 may further comprise a second bone fixation element 410 for fixing the intramedullary device 402 at a desired position within the medullary canal of the bone 406. The intramedullary device 402 may be substantially similar to the intramedullary device 102 including a longitudinal body 412 and a head 414 attached to a proximal end 416 thereof. The head 414 is adapted and configured to engage the plate 404 and may include for example, a plurality of recesses 418 for engaging the plate 404, each of the recesses 418 being configured and adapted to accommodate a height of the plate 404. The longitudinal body 412 of the intramedullary device 402 may include at least one opening 420 for accommodating the second bone fixation element 410. The at least one opening 420 may extend laterally through the longitudinal body 412 to accommodate the second bone fixation element 410 in a manner similar to that described in regard to the previous embodiment.

As shown in FIG. 12, the plate 404 includes a first portion 422 and a second portion 424, which are attached to one another via a neck portion 426. The first portion 422 may be substantially similar to the plate 104 of the system 100. The first portion 422 may be substantially U-shaped such that a pair of arms 430 extend from a midsection 428. A space 432 between the pair of arms 430 is sized and shaped to accommodate the head 414 of the intramedullary device 402 such that an inner surface 434 of the midsection 428 engages one of the plurality of recesses 418.

The second portion 424 is connected to the midsection 428 of the first portion 422 such that a plane of the first portion 422 is substantially perpendicular to the second portion 424. The second portion 424 includes a first surface 436, which faces the bone 406, and a second surface 438, which faces away from the bone 406. The second portion 424 may be a plate for fixing a fracture of the bone 406 externally, while the first portion 422 is inserted into the bone 406 to provide a support of the joint zone. Thus, in an operative position, the first portion 420 is inserted into the bone 406 at an angle relative to the head 414 of the intramedullary device 402 such that the inner surface 434 of the midsection engages one of the plurality of recesses 418 of the head 414 and the first surface 436 of the second portion 424 abuts a surface of the bone 406. The second portion 424 includes at least one opening 440 for accommodating the first bone fixation element 408 such that the second portion 424 may be fixed to the bone 406. Since the second portion 424 may externally fix a fracture of the bone 406, it will be understood by those of skill in the art that the second portion 424 may include more than one opening 440. Accordingly, it will also be understood by those of skill in the art that the system 400 may include more than one first bone fixation element 408 for insertion into the opening 440. The first bone fixation element 408 may be any fixation element such as, for example, a screw, blade or pin.

The second bone fixation element 410 may be substantially similar to the second bone fixation element 110 of the system 100. The second bone fixation element 410 is insertable through the at least one opening 420 to fix the intramedullary device 402 within the medullary canal of the bone 402. Thus, it will be understood by those of skill in the art that the second bone fixation element 410 may be any fixation element such as, for example, a screw, blade or pin. It will also be understood by those of skill in the art that the system 400 may include more than one second bone fixation element 410.

As shown in FIGS. 13-19, a surgical technique for applying the system 100, according to an exemplary embodiment of the present invention includes inserting the intramedullary device 102 into the medullary canal of the bone 106, using a guiding device 10 coupled to a proximal end of the device 102, as shown in FIG. 13. The intramedullary device 102 may be inserted into the medullary canal of the bone 106 via a fracture zone of the bone 106, as shown in FIG. 14. The longitudinal body 112 of the intramedullary device 102 is positioned within the medullary canal, while the head 114 of the intramedullary device 102 is positioned substantially within a head portion of the bone 106. The guiding device 10 may additionally hold the intramedullary device 102 relative to the bone 106 until the surgical procedure has been completed. Once the intramedullary device 102 has been positioned at a desired location within the medullary canal of the bone 106, the bone 106 is prepared for implantation of the plates 104, as shown in FIG. 15. For example, the bone 106 may be chiseled to create space for the insertion of the plate 104, as would be understood by those skilled in the art. A chisel 12 may be attached to the guiding device 10 to chisel the bone 106.

Figure 19:
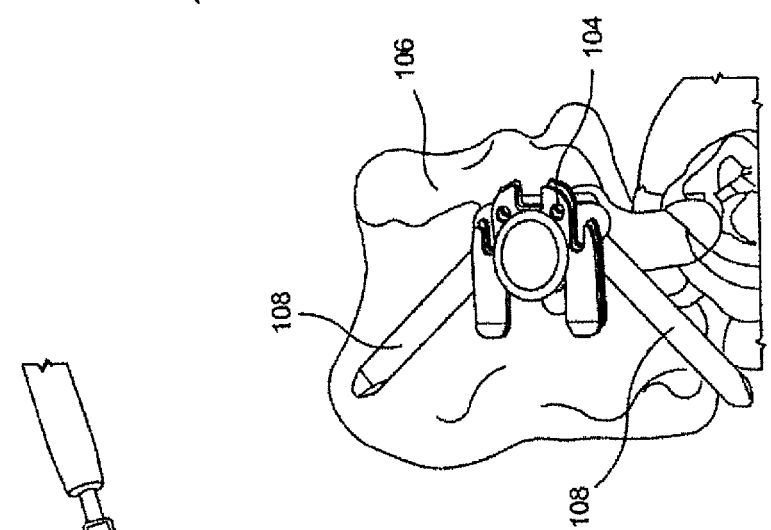
FIG. 19 illustrates perspective view of the embodiment of the intramedullary device of FIG. 13 with the guiding device removed.
Figure 17:
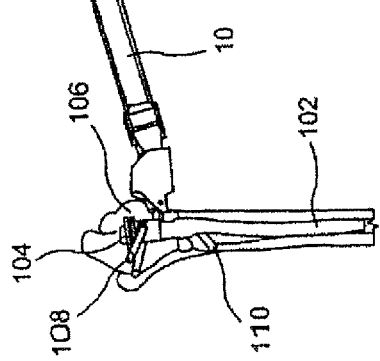
FIG. 17 illustrates a side view of the embodiment of the intramedullary device of FIG. 13 with the first and second bone fixation elements inserted.

Once a space for the plate 104 has been created, the plate 104 is inserted into the space to be coupled to the bone 106, as shown in FIG. 16, providing a wide support for the joint zone. The plate 104 may be inserted into the bone 106 until the inner surface 134 of the midsection 128 engages one of the plurality of recesses 118. The plate 104 may be inserted into the bone 106 using a plate guiding device 14, which may also be attachable to the guiding device 10 such that the plate 104 may be inserted in a desired orientation relative to the intramedullary device 102. It will be understood by those of skill in the art that more than one plate 104 may be coupled to the bone 106 as desired to treat a particular fracture. It will also be understood by those of skill in the art that the plate 104 should be implanted such that the plate 104 does not block the first opening 122. After implantation of the plate 104, the first bone fixation element 108 and the second bone fixation element 110 are inserted through the first and second openings 122, 124, respectively, as shown in FIG. 17. The first bone fixation element 108 is preferably passed through the first opening 122 into to couple a target fractured portion of bone to the shaft of the bone 106. The second bone fixation element 110 is passed through the second opening 124 into a portion of the shaft of the bone 106 to fix the intramedullary device 102 at a desired position within the medullary canal, as shown in FIGS. 18 and 19.

Although the surgical technique has been described with respect to the system 100, it will be understood by those of skill in the art that a substantially similar surgical technique may be used for the system 400. Additionally, for the system 400, it will be understood by those of skill in the art, that subsequent to the implantation of the plate 404, the first bone fixation element 408 will be inserted through the opening 440 of the plate rather than the intramedullary device 402.

It will be apparent to those skilled in the art that various modifications may be made in the present invention without departing from the spirit or the scope of the invention. Thus, it is intended that the present invention cover modifications and variations of this invention provided that they come within the scope of the appended claims and their equivalents.

What is claimed is:

1. A system for fixing a fracture near a joint of a bone, comprising:
    an intramedullary device including a longitudinal body and a head, the longitudinal body extending from a proximal end to a distal end, the head being attached to the proximal end of the longitudinal body; and
    a plate implantable into a portion of the bone to provide support to a joint zone, the plate being engageable with the intramedullary device, wherein
        A) the plate is substantially U-shaped; and
        B) the plate includes a midsection and a pair of arms extending from the midsection, the pair of arms forming a space therebetween, the space sized and shaped to accommodate the head of the intramedullary device, the head of the intramedullary device including a longitudinal axis and a plurality of recesses, each recess extending about at least a portion of a perimeter of the head substantially perpendicular to the longitudinal axis of the head, the recess being sized and shaped to accommodate an inner surface of the plate, wherein the inner surface of the plate is sized and shaped to be accommodated in one of the plurality of recesses to lock the plate in a desired position relative to the head.

2. The system according to claim 1, the plate including a first portion implantable into the bone and a second portion fixable to a surface of the bone, the first portion being substantially U-shaped and including a midsection and a pair of arms extending from the midsection, the pair of arms forming a space therebetween to accommodate the head of the intramedullary device, the second portion being sized and shaped to fix a fracture of the bone.

3. The system according to claim 2, wherein the first portion of the plate lies in a plane substantially perpendicular to a plane in which the second portion is lying.

4. The system according to claim 2, the second portion including a plurality of openings, the plurality of openings sized and shaped to accommodate bone fixation elements therethrough.

5. The system according to claim 1, wherein the intramedullary device has one or more openings extending laterally through the head of the intramedullary device.

6. The system according to claim 5, further comprising a bone fixation element insertable into the opening of the intramedullary device to fix a fracture of the bone.

7. The system according to claim 6, the bone fixation element being a locking head screw and the opening of the intramedullary device having a thread.

8. The system according to claim 5, wherein the intramedullary device has at least two openings whose central axes are not parallel to each other.

9. The system according to claim 8, wherein the central axes flare outwardly or converge for providing support to the joint surface.

10. The system according to claim 1, wherein the plate has an upper and a lower surface together having a surface area of 190 to 320 $mm^2$.

11. The system according to claim 1, wherein the plate has, measured in a plane of the plate, a minimum diameter of two times the diameter of the intramedullary device.

12. The system according to claim 1, wherein the plate has means for clipping the plate to the intramedullary device.

13. The system according to claim 12, wherein the pair of arms of the plate is configured as a snap-on mounting.

14. The system according to claim 13, wherein the snap-on mounting includes a circlip ring.

15. The system according to claim 1, wherein the system comprises several plates engageable with the intramedullary device on different heights of the intramedullary device.

16. The system according to claim 15, wherein the several plates include arms oriented in different directions.

17. The system according to claim 1, wherein the intramedullary device is an intramedullary nail.

18. The system according to claim 17, wherein the intramedullary nail includes one or more transverse locking holes.

19. The system according to claim 1, wherein the plate has an upper and a lower surface together having a surface area of 210 to 270 $mm^2$.

20. The system according to claim 1, wherein the plate has, measured in a plane of the plate, a minimum diameter of three times the diameter of the intramedullary device.

21. A method, comprising:
    inserting an intramedullary device into a medullary canal of the bone via a fracture zone of the bone, the intramedullary device including a longitudinal body and a head, the longitudinal body extending from a proximal end to a distal end, the head being attached to the proximal end of the longitudinal body;
    implanting a substantially U-shaped plate, including a midsection and a pair of arms extending from the midsection, the pair of arms forming a space therebetween, into the bone so that the pair of arms forming a space therebetween engagingly accommodate the head of the intramedullary device, wherein the implanting includes selecting one of a plurality of recesses in the head and securing the U-shaped plate to the selected recess.

22. The method according to claim 21, wherein the plate is clipped or secured to the intramedullary device.

23. The method according to claim 21, wherein several plates are engaged with the intramedullary device on different heights of the intramedullary device.

* * * * *